United States Patent [19]

Mouchawar et al.

[11] Patent Number: 5,830,236
[45] Date of Patent: Nov. 3, 1998

[54] SYSTEM FOR DELIVERING LOW PAIN THERAPEUTIC ELECTRICAL WAVEFORMS TO THE HEART

[75] Inventors: Gabriel Mouchawar, Newhall; James D. Causey, III; Mark W. Kroll, both of Simi Valley, all of Calif.

[73] Assignee: Pacesetter, Inc., Sylmar, Calif.

[21] Appl. No.: 741,184

[22] Filed: Oct. 29, 1996

[51] Int. Cl.$^6$ ............................................. A61N 1/39
[52] U.S. Cl. ............................................................ 607/5
[58] Field of Search ..................................... 607/5, 7

[56] References Cited

U.S. PATENT DOCUMENTS

| | | | |
|---|---|---|---|
| 4,403,614 | 9/1983 | Engle et al. | 607/5 |
| 5,318,591 | 6/1994 | Causey, III et al. | 607/7 |

*Primary Examiner*—William E. Kamm

[57] ABSTRACT

A system for delivering low pain cardioversion shocks to the heart wherein the system provides a waveform to the heart for cardioversion purposes to result in less stimulation of sensory nerves surrounding the heart. In one embodiment, the system includes a controller and a plurality of controlled switches that can be configured so that the heart receives a waveform through one or more resistors from a capacitor. The controller is configured to manipulate the switches so that the waveform that is applied to the heart is applied for more than 10 milliseconds so that the ratio of stimulation of the cardiac cells to the stimulation of sensory cells is approximately one. In another embodiment, the controller configures the switches so that a first capacitor discharges to charge a second capacitor through a resistor wherein the second capacitor is in parallel with the heart. The heart then sees a waveform that inverse exponentially rises to a peak value over a time period selected to reduce stimulation of the sensory nerves.

11 Claims, 4 Drawing Sheets

SYSTEM FOR DELIVERING LOW PAIN THERAPEUTIC ELECTRICAL WAVEFORMS TO THE HEART

This application claims the benefit of U.S. Provisional Application(s) No.: 60/020,379 Jun. 25, 1996.

FIELD OF THE INVENTION

The present invention relates to implantable electrical devices and, more particularly, concerns a system that is capable of providing therapeutic electric shocks to the heart of a patient wherein the therapeutic electric shock is configured to reduce the amount of pain experienced by the patient.

BACKGROUND OF THE INVENTION

Implantable electrical devices, including pacemakers and implantable cardioverter-defibrillators (ICD's), are now commonly used in medical practice. These devices are implanted into a patient's body and they provide periodic electrical stimulus, i.e., therapeutic shocks, to the heart to regulate heart function. Typically, pacemakers and ICD's have one or more electrodes that are positioned within the chambers of the heart to deliver the therapeutic shocks.

Implantable cardioverter-defibrillators are an example of a commonly implanted therapeutic device. These devices serve basically two functions. Specifically, the device is configured to be able to provide a high intensity shock to the heart when a control system associated with the ICD detects that the heart is in a state of ventricular fibrillation. The therapeutic shock that is applied to the heart is comprised of a waveform that is configured to be able to end the ventricular fibrillation of the heart and restore the heart to a normal sinus rhythm. Another function that the ICD performs is that of a cardioverter wherein the ICD provides therapeutic shocks to correct ventricular tachycardia or atrial flutter or fibrillation and restore the heart into a normal sinus rhythm or perform shock on T-wave induction. The ICD can also provide therapeutic shocks to correct such conditions as atrial fibrillation. "Shock on T-wave" induction is a function in which a moderate energy shock is delivered during the heart's T-wave to actually cause ventricular fibrillation. This then allows for the testing of the sensory and defibrillation function of the implanted device.

With the typical ICD's of the prior art, the same waveform is applied to the heart regardless of whether the heart is experiencing ventricle fibrillation or atrial fibrillation or ventricle tachycardia. The waveform that is used is generally a biphasic waveform such as the waveform illustrated in FIG. 2. This waveform typically has a peak positive voltage of 750 volts which then exponentially decays to 250 volts at which time a negative voltage is applied to the heart that has a peak voltage of −250 volts which then subsequently exponentially decays to approximately −100 volts. While this waveform is particularly effective at ending episodes of ventricular fibrillation, when this waveform is applied to the patient for cardioversion purposes, to correct ventricle tachycardia or to correct atrial fibrillation, or for shock on T-wave induction, the patient is usually conscious and consequently experiences a very painful sensation associated with the shock. However, when the waveform is being applied for fibrillation purposes the patient is usually (e.g., approximately 70% of the time) rendered unconscious by the fibrillation of the heart and, therefore, does not experience the same painful sensation.

It will be appreciated that a patient equipped with an ICD is likely to experience multiple events of the heart that would require cardioversion. Consequently, the patient is likely to experience very sudden painful shocks as a result of the ICD correcting a cardioversion event at periodic intervals while equipped with the ICD. These very painful shocks have a very serious effect of lowering the quality of life of the patient with the ICD.

In the prior art, there are some implantable electrical devices that are capable of varying the waveform of the therapeutic shock that is applied to the heart. For example, U.S. Pat. No. 5,184,616 to Weiss is an example of an implantable electrical device that is capable of generating varying arbitrarily shaped waveforms to control arrhythmia within the heart. While the device disclosed in this patent is capable of providing different waveforms, this patent fails to disclose a system that is capable of providing a waveform for cardioversion purposes that is specifically configured to successfully end the cardioversion event while minimizing the pain experienced by the patient.

Further, in the existing literature, it is known that different therapeutic waveforms have been used to reduce the pain experienced by the patient in external pacing applications. For example, external non-invasive techniques for stimulation of the heart have been described in an article entitled "*Resuscitation of the heart in ventricular standstill by external cardiac stimulation*" by P. M. Zoll *N. Engl. J. Med.* 247:768 (1952) and in an article entitled "*External noninvasive electrical stimulation of the heart*" by P. M. Zoll, R. M. Zoll and A. H. Belgard *CRC Crit. Care Med.* 9:393 (1981). These articles have described techniques for external stimulation of the heart and have discussed the waveforms that are best suited for external stimulation. A similar, non-invasive pacemaker is described in U.S. Pat. No. 5,018,522 to Rahul that applies a therapeutic shock through the skin that has a waveform that is configured to reduce the amount of pain experienced by the patient. However, in the prior art, there is no teaching of an implantable cardioverter-defibrillator that is capable of automatically adjusting the configuration of the waveform that is applied to the heart to decrease the pain experienced by the patient.

Hence, there is a need for an implantable electrical device that is able to provide both therapeutic shocks that are configured to end a fibrillation episode and also therapeutic shocks that are configured to end a cardioversion episode wherein the cardioversion shock is further configured to reduce the pain experienced by the patient. To this end, there is a need for an implantable electric device that does not require a significant amount of additional circuitry in order to be able to achieve this goal. It will be appreciated that with all implantable electrical devices, the size and complexity of the device should be minimized in order to reduce the invasiveness of the implantation procedure and also to enhance the reliability of the device.

SUMMARY OF THE INVENTION

The aforementioned needs are satisfied by the implantable electrical device of the present invention which includes a controller that receives signals indicative of the heart function and provides output control signals to an output circuit that provides therapeutic shocks to the heart. Preferably, the output circuit can be configured to provide a first shock suitable for defibrillation purposes or a second shock suitable for purposes such as cardioversion in response to signals from the controller. In particular, the waveform of the second shock is configured to result in significantly less pain experienced by the patient than the pain that is felt by the patient when the first shock is provided.

In particular, the applicant has initially determined that the response of sensory cells surrounding the heart is significantly faster than the response of cardiac cells. Specifically, high peak voltage waveforms, when applied to the heart, are much more likely to stimulate sensory cells relative to cardiac cells. Consequently, in one embodiment, the ICD of the present invention is configured so as to reduce the peak voltage of the second shock so as to reduce the ratio of response of the sensory cells to the cardiac cells.

The applicant has also determined that sensory cells are less likely to be stimulated for longer time period waveforms. Consequently, in another embodiment, the present invention is configured so as to provide a second shock that is of sufficient duration to reduce the ratio of stimulation of sensory cells to cardiac cells.

Figure 1:
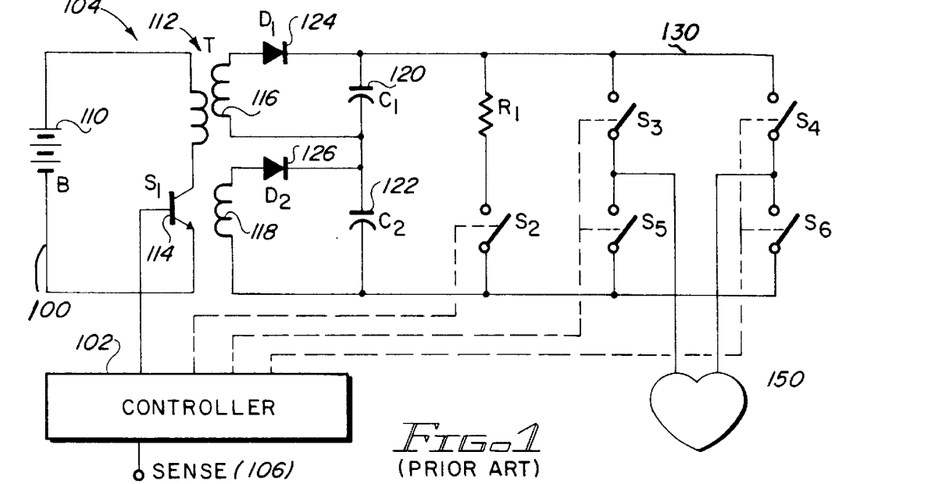
FIG. 1 is an exemplary electrical schematic of an ICD of the prior art.
Figure 2:
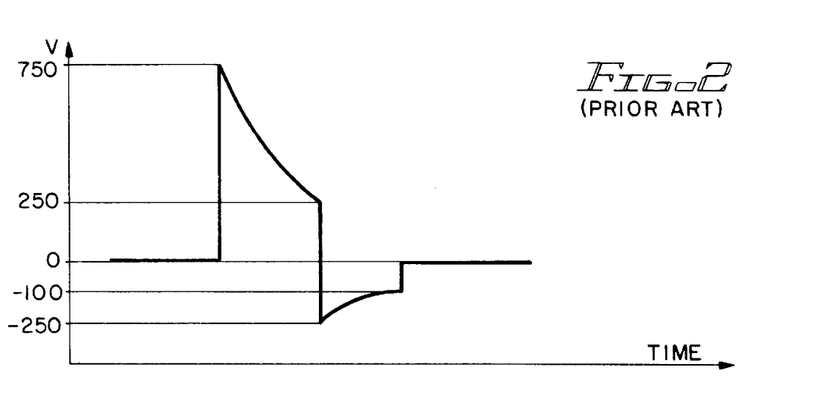
FIG. 2 is an exemplary waveform of a defibrillation shock produced by the circuit of FIG. 1.

More particularly, in one embodiment of the present invention, the output circuit of FIG. 1 includes a first and a second capacitor that are configured to be able to provide the biphasic fibrillation shock of FIG. 2 to the heart. The output circuit also includes a plurality of controllable switches, such as SCR's, MOSFET's, or I.G.B.T.'s that are capable of configuring the output circuit so that the second capacitor is charged via the first capacitor through a resistor, such as a dump resistor, and so that the second capacitor is in parallel with the heart. Consequently, as the second capacitor is charged, the heart sees a voltage waveform that has an inverse exponential rise wherein the time constant for the inverse exponential rise is determined by the value of the resistor and the two capacitors. These values are preferably selected so that the rise time is on the order of three to four milliseconds between a minimum value and a maximum value wherein the maximum value is selected to match that of the cardiac cells. This results in the cardiac cells being stimulated to approximately the same extent that the sensory cells would be stimulated. Consequently, the pain experienced by the patient for cardioversion shocks is reduced as there is less stimulation of the sensory cells located in the path of the cardioversion current, while still achieving the desired cardioversion. In this patent application cardioversion can include all non-defibrillation therapeutic shocks including shocks provided for regulation of ventricular tachycardia, atrial flutter, atrial fibrillation or shock on T-wave induction.

In another embodiment, the voltage is applied to the heart from a defibrillation capacitor with a resistor that is positioned in series with the heart. This results in a long duration therapeutic shock, e.g., on the order of 50 volts for greater than 10 milliseconds, being applied to the heart which results in a lower ratio of stimulation of the sensory cells to the cardiac cells. In this embodiment, there is a controllable switch in parallel with the resistor that shorts out the resistor which can therefore be used to provide a defibrillation shock to the heart wherein the entire voltage of the capacitor is applied directly to the heart. In yet another embodiment, the heart is supplied the voltages via a controllable H-bridge circuit and there is a resistor that is positioned in parallel to the heart during certain configurations of the H-bridge. Alternatively, the switches forming the H-bridge can be configured to short out the resistor so that the entire voltage of the defibrillation capacitor is applied to the heart for defibrillation purposes.

The ICD in this embodiment is therefore capable of selectively applying a defibrillation shock or a cardioversion shock to the heart wherein the output circuit can be configured so that the cardioversion shock is less likely to stimulate the sensory cells in embodiment, the cardioversion shock has a longer duration so that the cardiac cells are as likely to be stimulated as the sensory cells. This results in less stimulation of the sensory cells which results in lower pain experienced by the patient.

Alternatively, in a second embodiment, a low peak voltage is applied to the heart which is configured to rise to a value configured to stimulate the heart without excess stimulation of the sensory cells.

It will be appreciated that the present invention can be achieved by modifying a defibrillation output circuit to include a controller and controllable switches wherein the controllable switches are capable of providing the desired longer time period cardioversion shock. These and other objects and advantages of the present invention will become more fully apparent from the following description taken in conjunction with the accompanying drawings.

DETAILED DESCRIPTION OF THE PREFERRED EMBODIMENT

Reference will now be made to the drawings wherein like numerals refer to like parts throughout. The advantages of the present invention will become more fully apparent based upon an understanding of the operation of ICD's of the prior art. Consequently, the operation of a typical prior art ICD and the waveform that it produces is initially described in reference to FIGS. 1 and 2.

In particular, FIG. 1 illustrates a conventional ICD 100 of the prior art that is implanted to regulate the function of a heart 150 of a patient. In particular, the typical ICD 100 of the prior art includes a controller 102 and an output circuit 104. The controller 102 preferably receives signals indicative of the function of the heart 150 via a sense input 106 and uses these signals to configure the output circuit 104 to provide an appropriate output signal to the heart 150. Generally, the sense input 106 is comprised of one or more pacing leads that are implanted in the heart 150 that are configured to be able to sense the heart function when not providing a pacing pulse.

The circuit 104 operates as follows: the output circuit 104 generally includes a battery 110 that provides a voltage to the primary winding of a transformer 112 in response to the controller 102 toggling the switch 114 between on and off positions. This results in two secondary windings 116 and 118 respectively charging two capacitors 120 and 122 via two diodes 124 and 126. When these capacitors are charged, the controller 102 induces the switches of an H-bridge 130 to close so as to apply a waveform, such as the waveform illustrated in FIG. 2, to the heart. In particular, the controller preferably initially induces the switches S3 and S6 to close which delivers the positive phase of the shock to the heart 150. Subsequently, the controller then induces the switches S4 and S5 to close to thereby induce the negative portion of the shock.

FIG. 2 illustrates the preferred defibrillation shock that is produced by the circuit of FIG. 1. In particular, when the switches S3 and S6 are enabled, a voltage of 750 volts is applied to the heart. This voltage exponentially decays to approximately 250 volts over approximately 4 milliseconds at which time the controller 102 activates switches S4 and S5 so that a −250 volt potential is applied to the heart 150. The waveform then decays from −250 volts to approximately −100 volts over approximately 2 milliseconds wherein the switches S4 and S5 are then opened. The waveform of FIG. 2 is recognized as being particularly well suited to correcting ventricular fibrillation of the heart 150.

While the waveform of FIG. 2 is particularly well suited for correcting fibrillation of the ventricle of the heart 150, this waveform when used for other purposes, e.g., for correcting ventricular tachycardia or for purposes such as atrial defibrillation and T-wave induction, results in the patient receiving a very painful sensation.

Figure 3:
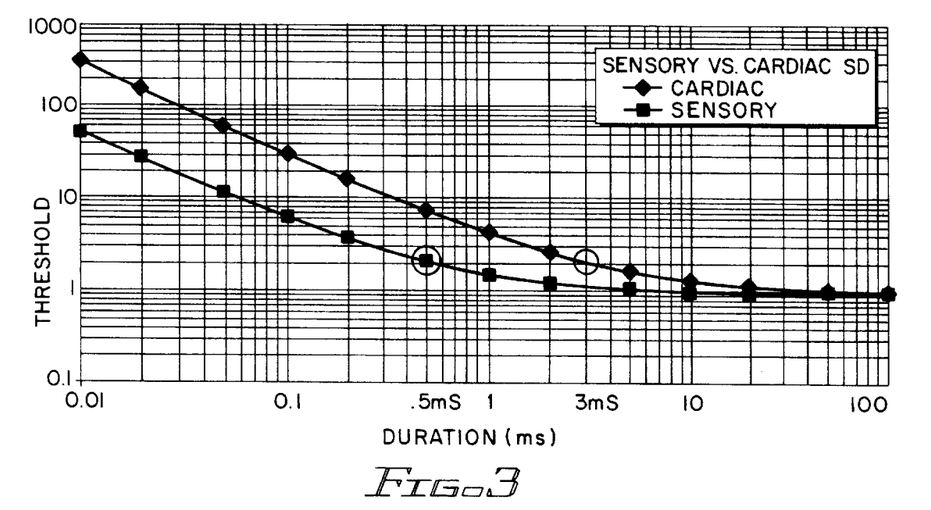
FIG. 3 is a diagram which illustrates the comparative strength duration curves of sensory nerve cells and cardiac nerve cells.

Through mathematical modeling, the applicant has determined that the pain that results from the typical prior art defibrillation shock can be largely explained by the quick response of sensory nerve cells. FIG. 3 is a chart of the normalized strength duration curves of the cardiac cells and the sensory cells which compares the threshold response of cardiac cells and sensory nerve cells for pulse stimuli of different durations. As shown in FIG. 3, the cardioversion/defibrillation chronaxie, i.e., the threshold pulse width on a strength duration curve at twice the rheobase value, for a cardiac cell occurs at approximately 3 milliseconds whereas the chronaxie for a sensory cell is in the range of 0.2 to 0.5 milliseconds. Consequently, the sensory cells respond much faster than the cardiac cells in response to an applied therapeutic shock. These time constants are well known. The time constants for cardiac cells are on the order of 3–4 milliseconds for shocks. However, the typical sensory cell has a time constant on the order of 200–500 $\mu$S. Thus, the sensory cells respond approximately 6–20 times faster than the cardiac cells.

Figure 4:
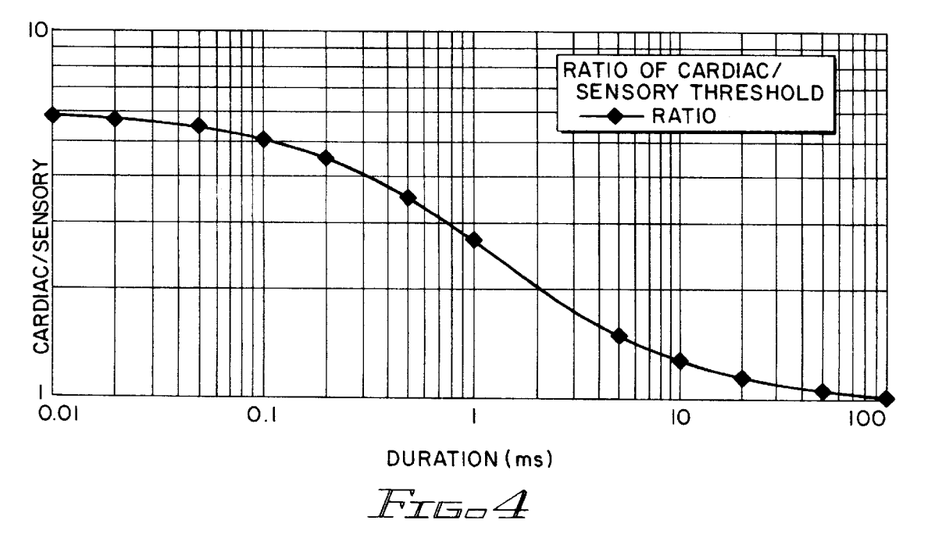
FIG. 4 is a diagram which illustrates the ratio of the threshold value for cardiac cells versus the threshold value for sensory cells in response to an applied electrical signal over time.

Further, as illustrated in FIG. 4, it is understood that if a ratio is calculated for the cardiac/sensory thresholds shown in FIG. 3, that this ratio has two asymptotic values. In particular, for a cardiac chronaxie of 3 milliseconds and sensory chronaxie of 0.5 milliseconds, the ratio between the cardiac/sensory threshold approaches a value of 6 at very short duration pulses. Therefore, for waveforms of very short duration, the sensory cells are six times more likely to be stimulated than the cardiac cells. Conversely, as illustrated in FIG. 4, as the duration of the therapeutic shock increases, e.g., is greater than 10 milliseconds, the ratio approaches an asymptotic value of 1. Therefore, therapeutic shocks that are greater than 10 milliseconds in duration, are equally likely to stimulate cardiac cells as they are to stimulate nerve cells. Therefore, applying a therapeutic shock that has a longer duration, e.g., 10 milliseconds or greater, will result in proportionally less sensory nerve stimulation while still stimulating cardiac cells as compared to shorter pulses.

Figure 5:
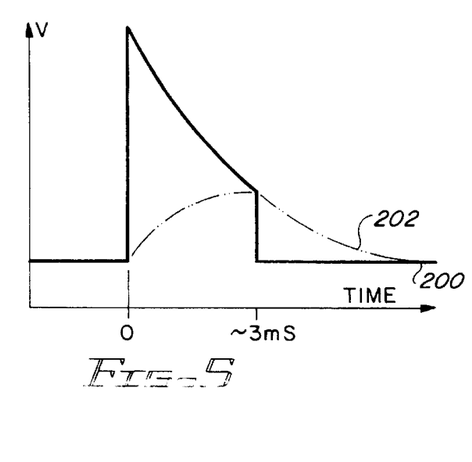
FIG. 5 is a schematic which illustrates the response of the cardiac cells in response to receiving the positive portion of the waveform of FIG. 2.
Figure 6:
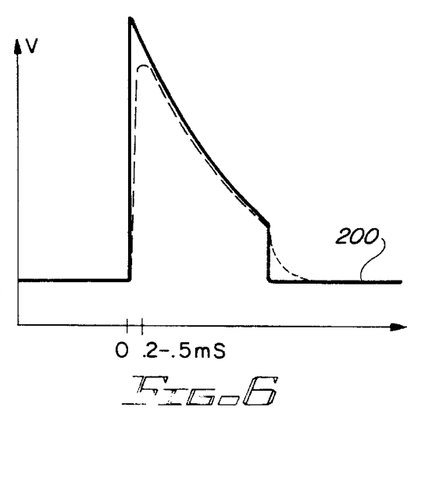
FIG. 6 is a diagram illustrating the response of sensory nerve cells in response to receiving the positive portion of the waveform of FIG. 2.

FIGS. 5 and 6 illustrate another phenomenon that has been identified by the applicant. In particular, in FIG. 5, the positive portion of the defibrillation waveform 200 (FIG. 2) is illustrated. The dashed line 202 illustrates the response of the myocardial cell. At approximately 3–4 milliseconds after the defibrillation waveform 200 has been applied, the myocardial cell fully responds. However, as illustrated in FIG. 6, in response to the therapeutic waveform 200, the sensory nerve cells, as indicated by the dotted line 204, have responded nearly simultaneously to the application waveform 200. Consequently, almost the entire positive waveform 200 of the therapeutic shock shown in FIG. 2 stimulates the sensory nerve cells even though the cardiac cells will not respond until the positive waveform is almost completed.

Thus, it can be said that the pain is determined by the peak voltage of the shock. Hence, when the defibrillation waveform of FIG. 2 is used for cardioversion purposes, the patient experiences a significant amount of pain as a result of the undesired stimulation of the sensory cells. Since the sensory cells are being stimulated without a corresponding stimulation in the cardiac cells, the patient is in effect experiencing a pain penalty as a result of using the defibrillation waveform for cardioversion purposes.

Figure 7A:
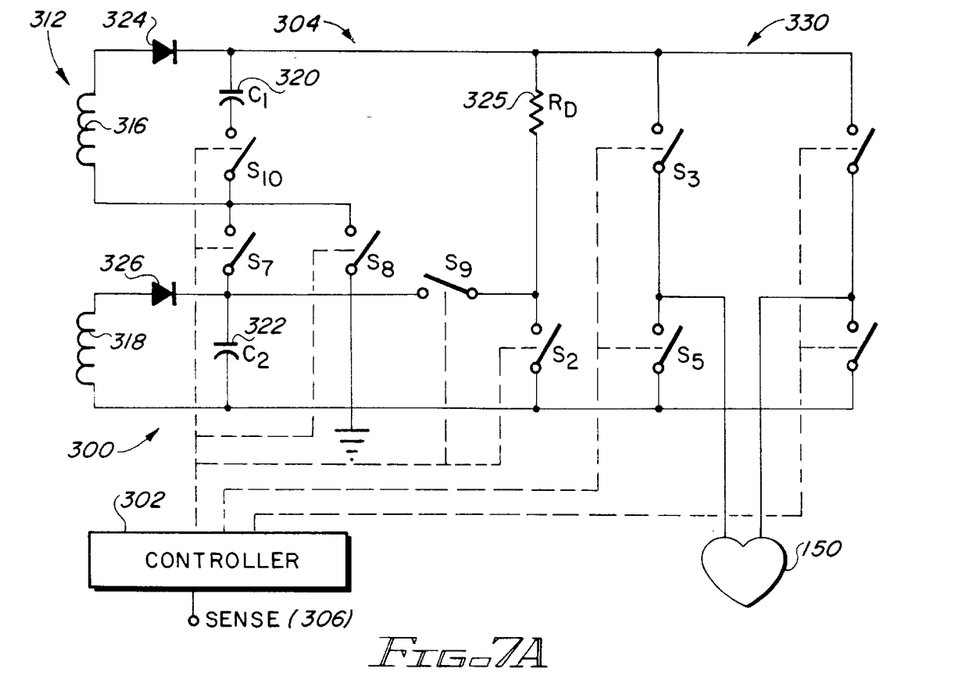
FIG. 7A is an electrical schematic illustrating a first embodiment of the ICD of the present invention.

FIG. 7A is an electrical schematic of one embodiment of an ICD 300 that is configured to apply a cardioversion waveform to the heart that is of the gentle, rounded shape so that the cardiac cells are stimulated while minimizing excess stimulation of the sensory cells surrounding the heart. FIG. 7A simply illustrates the output stage of an output circuit 304. The circuit 304 includes a battery 110 that feeds the primary winding of a transformer 312 in response to manipulation of a switch (not shown) similar to the transistor switch 114 shown in FIG. 1. This results in the secondary windings 316 and 318 charging a first capacitor 320 and a second capacitor 322 through diodes 324 and 326 respectively when a switch S10 is in a closed position. Once the capacitors 320 and 322 are charged, controllable switches S3–S6 in the H-bridge 330 and S7 and S10 can then be closed to apply the defibrillation waveform of FIG. 2 in the manner described above in reference to FIG. 1. Hence, the ICD circuit 300 is capable of applying a biphasic defibrillation waveform to the heart 150 of the patient.

However, the output circuit 304 also includes a plurality of switches S7–S10 that are controllable by the controller 302. In particular, the controller 302 manipulates the switches S7–S10 to apply the gentle, rounded cardioversion waveform 320 (shown in FIG. 7C) that is configured to stimulate the cardiac cells of the heart 150 while minimizing any excess stimulation of the sensory cells surrounding the heart 150. The switches S7–S10 are preferably comprised of SCR's or transistors that are operable by control signals emanating from the controller 302.

In particular, when the controller 302 receives a signal on the sense input 306 indicating the need for the cardioversion waveform 350, the controller opens the switch S10, which opens the circuit to capacitor 320. The controller 302 induces the primary winding of the transformer 312 to be energized from the battery 110 (FIG. 1). This results in only the capacitor 322 being charged via the diode 326. After the capacitor 322 is charged, the controller 302 then opens S7 and closes switch S8 which connects the capacitor 320 to ground. Further, the controller also closes a switch S9 and the switch S10 which connects the capacitor 320 to ground and also to the capacitor 322 through a resistor 325. The controller 302 also closes two of the switches in the H-bridge 330, i.e., switches S3 and S6, so that the equivalent circuit shown in FIG. 7B is produced.

In particular, the heart 150 is now in parallel with the uncharged capacitor 320 and the capacitor 322 in series with the resistor 325. This results in the capacitor 322 discharging to thereby charge the capacitor 320 through the resistor 325. It will be appreciated that the capacitor 320 is charged in an inverse exponential fashion as shown by the waveform 350 in FIG. 7C. In particular, the component values of the capacitors 322 and 320 and the resistor 325 are selected so that the waveform seen by the heart 150 charges for approximately 3 milliseconds to a threshold value that is selected to stimulate the cardiac cells of the heart 150. After three milliseconds, the controller 302 opens the switches S3 and S6 thereby removing the applied voltage to the heart 150.

Figure 7B:
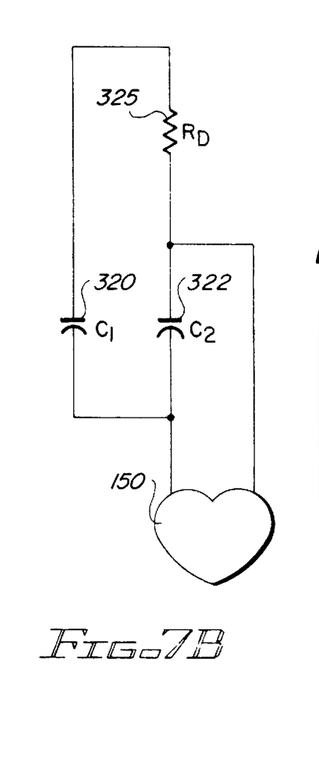
FIG. 7B is a schematic illustrating the equivalent circuit of the ICD shown in FIG. 7A when the circuit is configured to provide the low pain cardioversion shock.
Figure 7C:
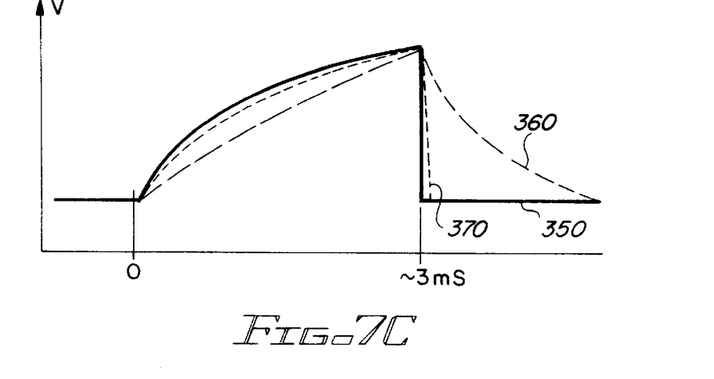
FIG. 7C is a diagram illustrating the positive portion of the cardioversion waveform produced by the circuit of FIG. 7A.

FIG. 7C illustrates that the waveform 350 produced by the equivalent circuit of FIG. 7B results in a stimulation of the cardiac cells as represented by waveform 360 and with the sensory cell response 370 more closely tracking the waveform 350. This results in a reduction in the stimulation of the sensory cells as compared to the defibrillation waveform 250 which further results in less pain experienced by the patient. Consequently, the myocardial cells of the heart 150 are adequately stimulated for cardioversion purposes but do not result in excess stimulation of the sensory cells.

It will be appreciated by reference to FIG. 7A that the ICD 300 of this embodiment is capable of providing both the waveform 250 of FIG. 2 and the waveform 350 of FIG. 7C. Further, the functionality of providing these two disparate waveforms is achieved through the addition of the controllable switches S7–S10. It will be appreciated that the ICD 300 achieves this greater functionality without requiring a significant amount of space for additional components.

In the embodiment shown in FIG. 7A, the resistor that is used to charge the capacitor 320 is the dump resistor 325. In the event that the charge in the capacitors 320 and 322 may want to be dumped without being applied to the heart, the controller is configured to enable the switches S2 and S10 and S7 while disabling the switches S8 and S9 which will result in the store charge in the capacitors 320 and 322 being dissipated across the resistor 325 in a manner and for purposes that are well understood in the art. It will be appreciated that, while the use of the dump resistor 325 as a resistor configured for applying the cardioversion waveform is efficient, two separate resistors can be used, one for dumping and one for producing the cardioversion waveform, without departing from the spirit of the present invention.

It will be further appreciated that the exact configuration of the waveform 350 (FIG. 7C) can be tuned by adjusting the value of the resistor 325. A typical value for this resistor 325 would be between 10–200 ohms. It will be further appreciated that the waveform 350 can be extended in length by opening and closing the switch S9 after the switches S3 and S6 are closed. This results in a pulsating current being applied to the capacitor 320 which then smooths (low pass filters) the waveform to increase the effective time constant and, hence, the duration. Further, a person of ordinary skill in the art will appreciate that the circuit of FIG. 7A can be modified slightly so that a biphasic voltage can be applied to the heart 150 with a similar inverse exponential rise on both the positive and negative sides of the waveform. This type of waveform can also be used for various beneficial therapeutic purposes.

Figure 8A:
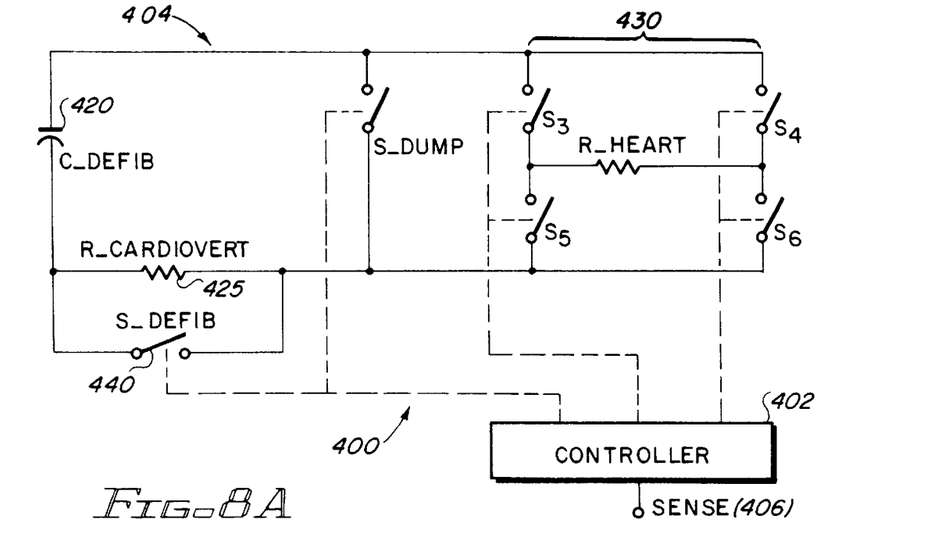
FIG. 8A is an electrical schematic of another embodiment of the ICD of the present invention.

FIG. 8A is a simplified schematic of another embodiment of an ICD 400 that is capable of providing both a defibrillation shock similar to the waveform shown in FIG. 2 and a longer duration cardioversion shock to the heart 150. In particular, the ICD 400 includes a controller 402, which receives a sense input 406 in the same manner as described above, and an output circuit 404. In FIG. 8A, the output circuit 404 includes one or more defibrillation capacitors 420 which are preferably charged in a similar manner as described hereinabove. Further, the output circuit 404 includes an H-bridge 430 comprised of switches S3–S6 that apply the therapeutic shock to the heart 150 which in FIG. 8A is represented by a resistor.

Figure 8B:
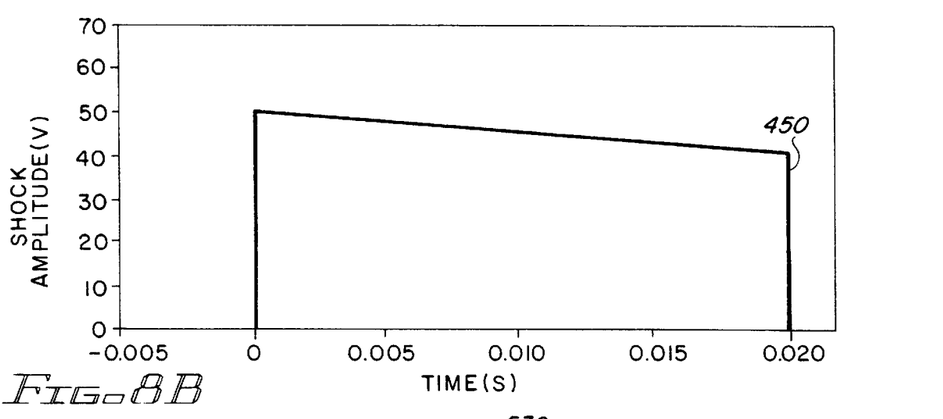
FIG. 8B is a diagram illustrating the waveform produced by the circuit of FIG. 8A.

A cardioversion resistor 425 is connected in series between the capacitor 420 and the H-bridge 430. Further, there is a defibrillation switch 440 that is connected across the resistor 425 so that when the switch 440 is closed by the controller 402, and the H-bridge is closed across the heart 150, a defibrillation waveform, such as the waveform 250 shown in FIG. 2, can be applied to the heart 150. Alternatively, when the H-bridge 430 is closed by the controller 402 manipulating two of the switches S3–S6 to apply the voltage in the capacitor 420 and the controller opens the switch 440, a cardioversion waveform 450 shown in FIG. 8B is applied to the heart 150.

In this embodiment, the capacitor 420 is capable of storing up to 750 volts. However, for a long duration pulse (e.g., a pulse of 10–20 milliseconds) only approximately 45 volts is needed to perform cardioversion. Consequently, the resistance of the cardioversion resistor 425 is selected so that the total voltage that is seen by the heart is approximately 40–50 volts. Further, the tilt or decline of the waveform seen by the heart is less as a result of the increase in resistance since the time constant of the discharge of the capacitor 420 is equal to the resistance of the heart 150 plus the resistance of the resistor 425 times the capacitance of the capacitor 420.

Therefore, a cardioversion waveform 450 can be applied to the heart 150 that is relatively long in duration with a gradual decrease in amplitude. This results in lowered stimulation of the sensory cells surrounding the heart while maintaining a sufficient degree of stimulation of the cardiac cells to result in cardioversion. In particular, reference to FIGS. 3 and 4 illustrate that at time lengths greater than 10 milliseconds, the waveform is as likely to stimulate the cardiac cells as the sensory cells. Consequently, applying the waveform 450, which is approximately 20 milliseconds long, results is less stimulation of sensory cells as the waveform 250 shown in FIG. 2. Consequently, the cardiac cells of the heart 150 are adequately stimulated for cardioversion purposes, but the pain experienced by the patient is decreased.

In the event that the controller 402 receives a signal via the sense input 406 indicating the need for a defibrillation shock, the controller 402 can close the defibrillation switch 440 and close the switches S3–S6 of the H-bridge 430 in the manner described above so that substantially the entire voltage of the capacitor 420 is applied across the heart in a waveform that is similar in shape to the waveform 250 shown in FIG. 2. Consequently, the ICD 400 is capable of providing both a defibrillation shock and a cardioversion shock wherein the cardioversion shock is configured to result in less pain to the patient.

Figure 9:
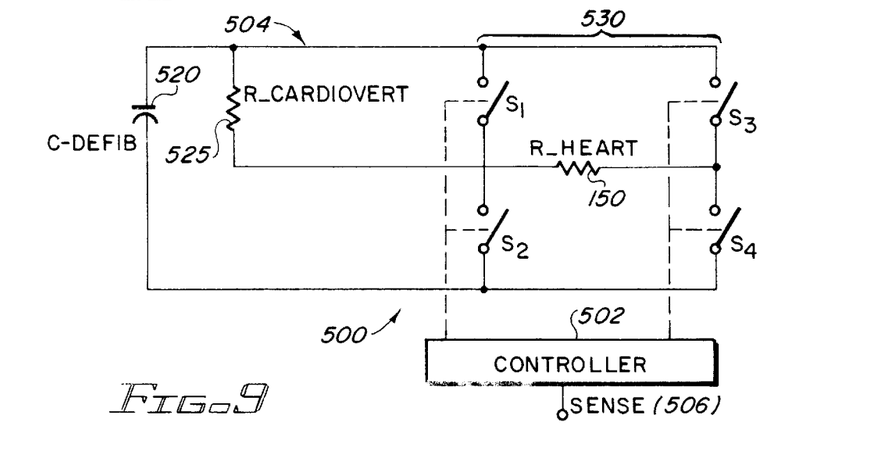
FIG. 9 is an electrical schematic illustrating yet another embodiment of the ICD of the present invention.

FIG. 9 is yet another embodiment of an ICD 500 that is capable of providing both a defibrillation shock of high amplitude and relatively shorter wave pulses and a cardioversion shock of comparatively low amplitude for a relatively long time period in the manner described above in conjunction with the description of the ICD 400 described in reference to FIGS. 8A and 8B. In particular, the schematic illustrated in FIG. 9 is a simplified schematic of an ICD 500 that includes a controller 502 which receives a sense input 506 in the same manner as described above. The ICD 500 includes an output circuit 504 which includes one or more defibrillation capacitors 520 that is charged in the manner described above. Further, there is an H-bridge 530 comprised of four switches, S1–S4, that are controlled by the controller 502 to apply the voltage to the heart 150. It will be appreciated that when the switches S1–S3 are open but the switch S4 is closed, then a cardioversion wave pulse similar to the wave pulse shown in FIG. 8B is applied across the heart 150. Alternatively, when the controller 502 receives a signal on the sense input 506 indicating that a defibrillation shock should be applied to the heart 150, the switches S1 and S4 can be closed thereby shorting out the cardioversion resistor 525 so that the positive portion of the shock can be applied to the heart 150. Subsequently, switches S3 and S2 are then closed so that the negative portion of the waveform 250 can be applied across the heart 150. In this manner, the ICD 500 is capable of providing both a biphasic defibrillation shock and a cardioversion shock that is configured to reduce the pain experienced by the patient depending upon the condition of the heart sensed by the controller 502. In both embodiments shown in FIG. 8A and FIG. 9, R-Cardiovert is the dump resistor.

From the foregoing, it should be apparent that the preferred embodiments of the present invention are capable of providing both fibrillation shocks and cardioversion shocks to the heart depending upon the conditions sensed by a controller. The cardioversion shock is configured so that the stimulation of the sensory cells surrounding the heart is minimized. This reduces the pain experienced by the patient during such activities such as ventricular cardioversion, atrial cardioversion, atrial defibrillation, defibrillation, and T-wave induction. This decrease in pain results in a higher quality of life for the patient.

Although the foregoing description of the preferred embodiments of the present invention has shown, described and pointed out the fundamental novel features of the invention, it will be understood that various omissions, substitutions and changes in the form of the detail of the apparatus as illustrated as well as the uses thereof, may be made by those skilled in the art, without departing from the spirit of the present invention. Consequently, the scope of the invention should not be limited to the foregoing discussion, but should be defined by the appended claims.

What is claimed is:

1. An implantable electrical device for providing therapeutic shocks to the heart, the device comprising:

controller for receiving a sense signal indicative of the operation of the heart and providing a plurality of output signals in response thereto; and an output circuit that provides therapeutic shocks to the heart wherein the output circuit comprises means for generating a first therapeutic shock having a first waveform to be applied to the heart, wherein said first waveform is characterized as having a first set of parameters including a first rise time, a first fall time, a first waveform duration, and a first level of stimulation, and wherein the first waveform is configured to accomplish ventricular defibrillation of the heart with the first level of stimulation, said output circuit further comprises means for generating a second therapeutic shock having a second waveform to he applied to the heart, wherein said second waveform is characterized as having a second set of parameters including a second rise time, a second fall time, a second waveform duration, and a second level of stimulation, each parameter of said second set of parameters being different than the corresponding one of the parameters of the first set of parameters, and wherein the second waveform is configured to perform cardioversion, with the second level of stimulation being less than the first level of stimulation to reduce thereby, pain experienced by the patient.

2. The device of claim 1, wherein the means for generating the first therapeutic shock generates the first waveform in the form of a biphasic waveform having a peak voltage of approximately 750 volts exponentially decaying to approximately 250 volts with a first fall time of approximately 4 milliseconds at which time a negative voltage of approximately −250 volts is applied to the heart that exponentially rises to −100 volts with a first rise time of approximately 2 milliseconds.

3. The device of claim 1, wherein the means for generating the second therapeutic shock generates the second waveform that exponentially rises from 0 volts to 50–375 volts with a second rise time of about 3 milliseconds.

4. The device of claim 1, wherein the second waveform is comprised of a waveform that is approximately 20 milliseconds long and has an initial peak starting voltage of approximately 50 volts that decays to an ending amplitude of 40 volts after the approximately 20 milliseconds.

5. An implantable electrical device for providing therapeutic shocks to the heart, the device comprising:

control means for determining an appropriate therapeutic shock to be applied to the heart in response to receiving a sense input indicative of the function of the heart; and means for generating and providing an appropriate therapeutic shock to the heart, said therapeutic shock having a waveform configured to accomplish cardioversion of the heart while reducing the amount of pain sensed by the patient, the waveform exponentially rising from 0 volts to 50–375 volts with a first rise time of about 3 milliseconds.

6. The device of claim 5, wherein the means for generating and providing an appropriate therapeutic shock generates a shock having a waveform with an initial peak starting voltage having a value of approximately 50 volts that decays to an ending value of 40 volts with a fall time of approximately 20 milliseconds dropping to a value of 0 volts immediately thereafter.

7. The device of claim 5, wherein the second waveform is comprised of a waveform that is approximately 20 milliseconds long and has an initial peak starting voltage of approximately 50 volts that decays to an ending amplitude of 40 volts after the approximately 20 milliseconds.

8. A method of correcting abnormal heart function using an implanted electrical device that provides therapeutic electric shocks to the heart, the method comprising the steps of:

sensing the function of the heart;

determining whether the heart is in a first condition that would require ventricular defibrillation or whether the heart is in a second condition that would require cardioversion or atrial defibrillation;

providing a first therapeutic shock to the heart when determining that the heart is in the first condition wherein the first therapeutic shock has a waveform that is configured to defibrillate the ventricles of the heart; and providing a second therapeutic shock to the heart upon determining that the heart is in the second condition, wherein the second therapeutic shock has a waveform that is configured to induce the atrial cardioversion or defibrillation of the heart and wherein the second waveform is configured to reduce the stimulation of sensory nerves surrounding the heart to thereby reduce the sensation of pain experienced by the patient.

9. The method of claim 8, wherein the step of providing the first therapeutic shock comprises providing a shock to the heart that has a biphasic waveform that has a peak voltage of approximately 750 volts that exponentially decays to approximately 250 volts after approximately 4 milliseconds at which time a negative voltage of approximately −250 volts is applied to the heart that exponentially decays to −100 volts after approximately 2 milliseconds.

10. The method of claim 9, wherein the step of providing the second therapeutic shock comprises providing a shock to the heart that has a waveform that has an inverse exponential rise from approximately 0 volts to 50–375 volts over approximately 3 milliseconds.

11. The method of claim 9, wherein the step of providing the second therapeutic shock comprises providing a shock to the heart that has a waveform that has an initial peak starting voltage of approximately 50 volts that decays to an ending amplitude of 40 volts after approximately 20 milliseconds.

* * * * *